United States Patent [19]

Schaldach

[11] Patent Number: 4,892,100

[45] Date of Patent: Jan. 9, 1990

[54] DEMAND PACEMAKER WITH PHYSIOLOGICAL CONTROL

[75] Inventor: Max Schaldach, Erlangen, Fed. Rep. of Germany

[73] Assignee: BIOTRONIK Mess- und Therapiegeräte GmbH & Co. Ingenieurbüro Berlin, Berlin, Fed. Rep. of Germany

[21] Appl. No.: 228,826

[22] Filed: Aug. 3, 1988

Related U.S. Application Data

[63] Continuation of Ser. No. 832,003, Feb. 24, 1986, abandoned.

[30] Foreign Application Priority Data

Feb. 22, 1985 [DE] Fed. Rep. of Germany ....... 3506789

[51] Int. Cl.⁴ ............................................. A61N 1/36
[52] U.S. Cl. ........................................... 128/419 PG
[58] Field of Search ................................. 128/419 PG

[56] References Cited

U.S. PATENT DOCUMENTS

| 4,052,991 | 10/1977 | Zacouto | 128/419 PG |
| 4,303,075 | 12/1981 | Heilman et al. | 128/419 PG |
| 4,543,954 | 10/1985 | Cook et al. | 128/419 PG |

Primary Examiner—William E. Kamm
Attorney, Agent, or Firm—Spencer & Frank

[57] ABSTRACT

Pacer control information adapting the pacers to an individual relating a physiological parameter obtained from a first sensor to a corresponding parameter obtained from a second sensor is stored in a memory for later address in response to a signal from the first sensor to provide the corresponding pacer control information to the pacer generator.

14 Claims, 3 Drawing Sheets

DEMAND PACEMAKER WITH PHYSIOLOGICAL CONTROL

This application is a continuation, of application Ser. No. 06/832,003, filed Feb. 24th, 1986, now abandoned.

BACKGROUND OF THE INVENTION

The invention relates to a cardiac pacemaker.

Physiologically controlled cardiac pacemakers are known in which the escape interval is regulated by a parameter derived from the body. In this connection, the article entitled "Ein Herzschrittmacher mit belastungsabhängiger Frequenzregulation" [A Cardiac Pacemaker With Stress Dependent Frequency Regulation] in the periodical Biomedizinische Technik [Biomedical Technology], No. 20, 1975, pages 225, 226, describes regulation by means of the respiration rate, while U.S. Pat. No. 4,467,807 discloses a pacemaker in which the base rate is regulated by the oxygen saturation.

Physiological control here means influencing the pacemaker so as to adapt the performance capability of the heart to the momentary requirements, i.e. particularly with respect to its basic rate which is independent of the prior patient specific regulation on the basis of electrical signals derived from the heart that were provided solely to avoid the simultaneous occurrence of stimulated pulses and spontaneous heart action.

Such pacemakers have the drawback that the relationship between the escape interval and the physiological parameter must either be given arbitrarily or the treating physician must adapt it to the individual patient in a time consuming series of experiments.

SUMMARY OF THE INVENTION

It is the object of the invention to simplify adaptation to the individual patient and thus make it possible that, in addition to initial adaptation to the individual stimulation requirements, the operating behavior of the pacemaker can continuously be brought up to date to correspond to changing demands for stimulation.

The invention is based on the realization that, in principle, the dependency of the heart rate from the physiological parameter selected for regulation of the stimulation interval remains essentially in effect under changing physical stresses, i.e. differences in performance requirements for the heart, regardless of whether the heart action is spontaneous or stimulated, so that after the respective "learning process" that heart frequency range which is traversed without pacemaker intervention during daily stresses on the patient is also available as a stimulation range even if spontaneous actions are absent.

For the case where a physiological parameter which itself depends on the type of chamber action (spontaneous or stimulated) is selected for a demand pacemaker, a preferred embodiment of the invention provides that difference between the parameter values for the two types of actions is compensated by a programmable correction value —possibly in dependence on the heart frequency—which is stored in a separate memory. The respective result is also attained if signal states defining the escape interval are stored in two different memory regions and these are called up differently depending on whether the preceding heart action was spontaneous or stimulated. In this way, it is possible for the escape interval determined on the basis of a physiological parameter to "run along" in the case of spontaneous action as well so that, in the absence of spontaneous action under stress, the patient receives an adequate stimulation rate.

Favorably, the last spontaneous frequency belonging to the momentary value of the parameter is stored in a corresponding memory and, upon the absence of spontaneous action, stimulation occurs with an escape interval corresponding to this frequency. The escape interval must here be dimensioned to be longer by a time difference than the rate corresponding to the spontaneous frequency, so that the system is able to follow a physiologically caused drop in frequency. This difference value is dimensioned in such a way that physiologically acceptable drops in frequency (d/dt) can take place without pacemaker intervention.

Thus, pacemaker operation is divided into a "calibration phase" during the occurrence of spontaneous action, in which a determination is made of the association of the parameter later to be utilized for regulating the stimulation rate with the natural heart frequency. Upon the later absence of spontaneous action, reference is then made to these stored values and the stimulation is continued corresponding to the natural heart rhythm, with this stimulation rate possibly being different from the natural rate. This has three reasons: either the stimulation rate is selected to be lower than the corresponding natural rate in each case so as to not unnecessarily intervene with artificial stimulation pulses; or it is selected to be higher (corresponding to the known hysteresis pacemaker operating with a fixed stimulation rate); or it is adequately adapted if the selected physiological parameter is a function of the activation state of the heart itself (e.g. QT interval) and if compensation is necessary.

In another preferred embodiment, the artificial stimulation rate is especially reduced in the specifically selectable "calibration phase" of a demand pacemaker equipped with the control according to the invention, so as to interrupt the natural heart behavior and the physiological course of the stimulation rate as little as possible by stimulation intervention.

According to another advantageous embodiment of the invention, such frequency ranges within the heart frequency range applicable for stimulation—as determined by separate examinations—can be excluded from stimulation so that in the case of the absence of spontaneous action, stimulation continues at a higher value than would correspond to the momentary value of the physiological parameter controlling the escape interval. Corresponding to the performance capability of the heart within the frequency range to be excluded, it can be provided that, in the presence of spontaneous action, the escape interval will initially be caused to follow the change in the physiological parameter. However, as soon as such spontaneous action is absent within the respectively applicable escape interval, stimulation is effected with a frequency above the frequency range to be excluded until the physiological parameter resets the escape interval to a value which belongs to a frequency below the frequency band to be excluded. In the case of greatly reduced performance capability of the heart within the frequency range to be excluded, it is possible to determine, by means of appropriate presetting from an external program, that a higher heart rate is generated by artificial stimulation even in the presence of spontaneous action, if the frequency lies within the frequency range to be excluded. Traversing of different escape interval ranges to be excluded as a function of the direction of change in the parameter takes place in the form of a hysteresis curve. These solutions have in common that the curve of the relationship between the physiological parameter used for the regulation and the pacemaker rate can be changed, in addition to the dependency resulting according to the invention, also manually by programming in individual cases.

For physiological parameters whose functional relationship to the heart frequency depends on the type of heart action (spontaneous or stimulated), the difference of the physiological parameters belonging to a momentary stimulation frequency can be determined for each case of spontaneous action and stimulated action if a change is made to the stimulation state after existing spontaneous actions (or vice versa).

Advantageously, the individual ideas of the solution can also be employed independently of one another and thus constitute separate solutions to be selected.

Preferably, physiological parameters such as the "QT intervals", the "systolic intervals," or pulses recorded by measuring the impedance in the heart (electroplethysmographically recorded pulses) are suitable for use.

The method described here can be used for pacemakers operating in various modes, with the single chamber pacemaker initially being preferred. If a change is made from ventricular to AV-sequential stimulation, it must be considered that in both cases separate functional dependencies must be considered, due to the different degree of chamber fill and the systolic intervals dependent on the stimulation mode, and these functional dependencies must be recorded in separate memories. Since otherwise conditions are analogous, it is possible to change from one mode to the other as desired—in each case with reference to corresponding stimulation frequencies—if conditions require.

Automatic adaptation of the stimulation frequency can be influenced by programming with respect to the frequency limits involved. For automatic adaptation corresponding to a "self-teaching process", which is also possible without running through a stress cycle under supervision of a physician on the basis of the changes in stress occurring during normal activity, the control range for stimulated frequencies would be adapted to that control range which would be covered if spontaneous actions were to occur.

The proper operation of the pacemaker, frequency controlled in the described manner, would be observable at any time without difficulty by the treating physician with utilization of the possibilities of two-way communications. Favorably, the external communications unit should here include an LCD display on which the functional dependency between the systolic time intervals and the stimulation frequency (distance between R waves) is graphically displayed the values stored within the pacemaker. The degree of linearity resulting here for the recorded dependencies for one or a plurality of stress cycles in the manner stated above gives the physician a clear picture of the possibilities of the method described here with respect to the respective patient. By considering curvatures in the depicted functional relationships, preferred frequencies can be manually programmed externally into corresponding memory locations reserved for this purpose as they appear favorable to the physician for the respective case. In view of the individual programmability of the functional dependency of the stimulation frequency on the basic rate for the demand function or even for a pacemaker without this characteristic, the most varied aspects of a disease can be given consideration.

BRIEF DESCRIPTION OF THE DRAWINGS

Advantageous features of the invention will be described in greater detail below together with a description of the preferred embodiment of the invention in reference to the drawing figures. It is shown in.

DESCRIPTION OF THE PREFERRED EMBODIMENT

The invention will be described below with reference to an embodiment which operates on the basis of regulation by means of the physiological parameter of "systolic intervals;" however, all other parameters known for "physiological pacemaker control" can also be utilized correspondingly.

Figure 1:
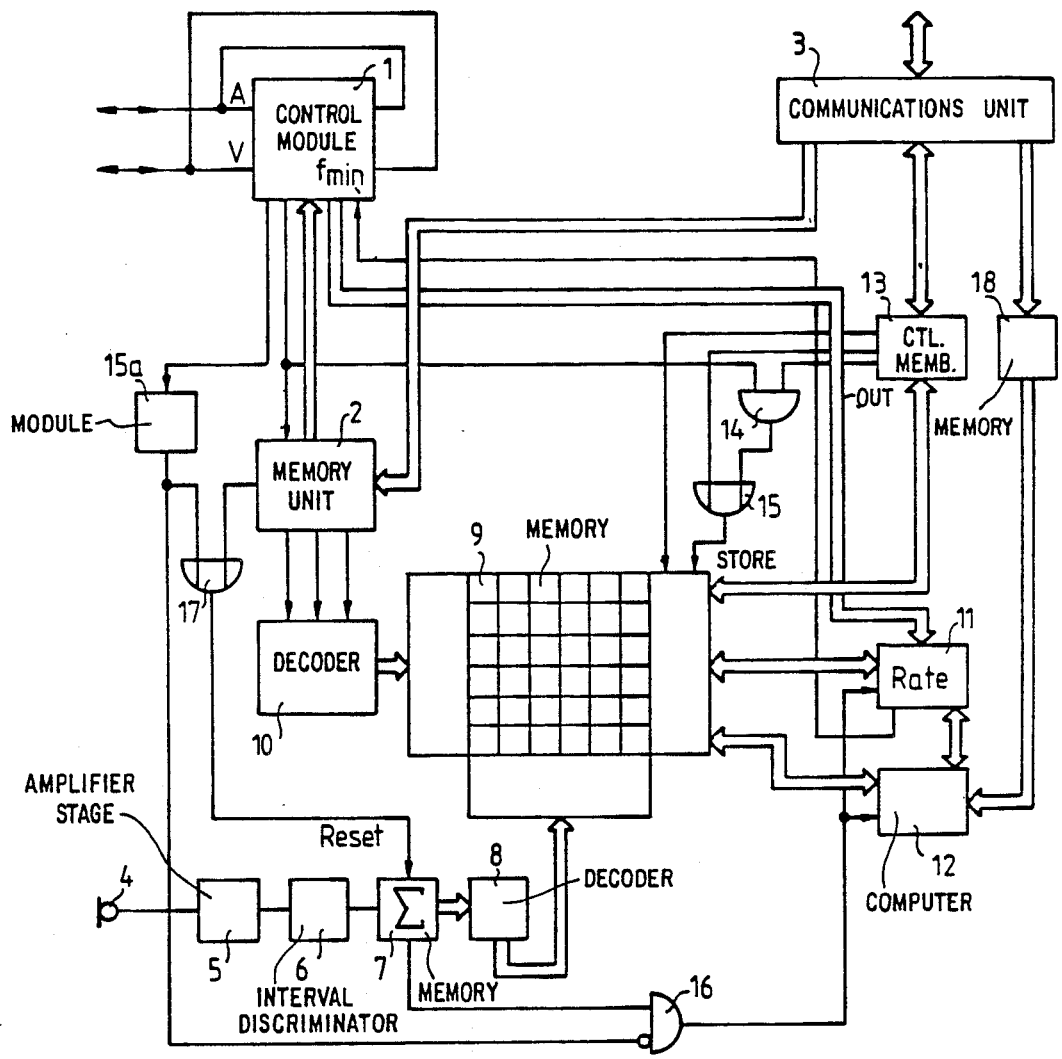
FIG. 1, a block circuit diagram of an embodiment of the cardiac pacemaker according to the invention.

The block circuit diagram of the embodiment illustrated in FIG. 1 includes a conventional programmable atrium and/or ventricle pacemaker with demand function. The corresponding inputs and outputs to connect it with the atrium and ventricle electrode, respectively, are marked "A" and "V". The operating state of the control module 1 for the basic functions of the pacemaker is determined by a memory unit 2 for the operating states (modes) of the pacemaker and this switching unit can be influenced by means of a communication unit 3 and external programming means. Switching unit 2 thus permits the setting of various operating states (VVI, DAT, DDD modes, etc.). In the illustrated pacemaker, the base rate or intervention frequency, which is set externally in prior art multiprogrammable pacemakers, can be programmed externally to go into the "physiological control" mode in which it adapts itself automatically to the patient's requirements by utilizing signals recorded from the patient's body.

As a particularity, the control module 1 illustrated here thus provides a terminal $f_{min}$ for influencing the basic frequency. The remaining modules shown in FIG. 1 are likewise combined in the implantable pacemaker housing.

The base rate, i.e. the escape interval, beginning with a preceding stimulated or spontaneous atrium or ventricle action and ending at the moment at which, in the absence of spontaneous action, stimulation occurs in the atrium or ventricle, can be changed by the remainder of the illustrated arrangement. The control is effected as a function of signals which are recorded acoustically within the patient's body, the left-ventricular systolic intervals. These signals are recorded by means of a microphone 4 which is designed as a vibration pickup and preferably includes a piezoceramic vibration transducer. The features of a vibration pickup suitable to implement in the invention will be described in greater detail with reference to FIG. 3. The output signal of the vibration pickup is fed to an amplifier stage 5 which filters out the relevant frequency ranges and emits an output signal if signals of the selected frequencies are present for a given minimum period of time. The frequencies involved are preferably frequencies as they have been used in the past for phonocardiological examinations of the systolic intervals.

The output signal of stage 5 is fed to an interval discriminator 6 which—started by the leading edge of a first input pulse—determines the time that expires until the next pulse, with the first arriving pulse causing a reset and the evaluation being limited to a given time window after which, if it was without success, the measuring device will again be reset. If, however, two successive pulses appear within the time window, the time interval between their leading edges is put out as a digital signal and fed to a mean value memory 7 which forms a mean from a number of successive time interval values and stores this mean value.

The mean value is reset when the set pacemaker mode is changed (including by external programming) or if the stimulation state changes (transition from operation with action from the patient's heart back to stimulated operation, etc.) so that the mean value formation of successive systolic intervals is made only for similar operating states.

The output signal of mean value memory 7 is transmitted to an address decoder 8, with the addresses evaluated by the decoder being quantized by the selected digitalization according to the smallest step increases of the digital values so that the resolution of the time intervals to be evaluated always forms the difference between two adjacent memory addresses. Additionally, the address decoder 8 converts the output signal of sum memory 7 in that it subtracts the minimum value of a systolic time interval to be evaluated from the digital input values and possibly adds additionally the address of the memory location (within a larger memory region). The memory 9 shown in FIG. 1 is organized in the form of a matrix, with the systolic time intervals addressing the columns while a further address decoder 10 which is influenced by operating mode memory 2 addresses the rows of the memory organized in the form of a matrix. In this way, it is accomplished that only the systolic time intervals for similar operating modes (spontaneous actions, ventricular or AV-sequential stimulation) are recorded. Upon a transition from one mode of operation to the other, mean value memory 7 is erased by way of its "reset" input and the mean value formation begins anew.

In an embodiment of the memory employing commercially available RAM elements, memory 9 will be configured in such a way that decoders 8 and 10 actuate different address lines, with both address signals forming a common binary address so that the address actuation coincides with that of customary microprocessor systems. The base rate included in the addressed memory values is transmitted by means of a base rate memory 11 into which they are taken over as buffer memory, with this value contained in the base rate memory determining the minimum stimulation frequency for the pacemaker circuit.

In this way a minimum stimulation rate is given as a function of the determined systolic time intervals and of the momentary mode of pacemaker operation and this stimulation rate corresponds physiologically to the determined systolic intervals. By initially setting up a table of the previously determined patient specific dependencies—as will be described below—the control is independent of further physiological dependencies which might influence the systolic time intervals if they have any connection with the base rate. If the determined intervals change, the base rate will gradually change as well, with the interval recorded to initiate the change not necessarily corresponding to that interval period which belongs to the target frequency to be set, unless the change in intervals to be considered until the target frequency is reached changes its sign. Thus, if deviations are noted, the illustrated control will slowly lead the stimulation frequency (also as a result of the operation of mean value memory 7) to the new physiologically required stimulation frequency, with the further interval changes to be traversed in the course of the approach not interfering with the realization of the final target frequency if the relationship between the recorded time interval and the associated pacemaker rate is unequivocal. The buffer memory 11 for the base rate is activated each time by an "evaluation" signal which is derived from mean value memory 7 and signals the arrival of a new systolic interval value. In this operation, it is assumed that all frequency values in memory 9 have been transmitted externally from communications unit 3, with the communications unit setting the pacemaker, by means of a control member 13 subject to external programming, into the "read-out" state so that each address from a systolic time interval reads out the associated value stored in memory 9.

In an operating mode identified by control member 13 via the output "out", if action from the heart is present (corresponding output of pacemaker member 1), the pacemaker operates with automatic storage in memory 9 of the spontaneous frequency belonging to certain systolic intervals so that these signals can also be utilized for stimulation that may become necessary later. The distance between two recorded identical spontaneous actions in the heart (within a physiologically justifiable range) is in this case transmitted by pacemaker member 1 to base rate memory 11 and is read into the respectively addressed memory location which in this case is associated, via operating mode addressing member 2, with action from the heart. In this case, the "store" input of memory 9 is linked, by means of an AND gate 14, with the "out" output of control member 13 and the output signal "spontaneous action" of module 1 of the pacemaker and the "store" input of memory 9 is actuated via an OR gate 15.

Moreover, on the basis of the signals from the heart recorded by pacemaker member 1, the latter performs a tachycardia (and/or extrasystole) and malfunction detection which is processed by means of a corresponding module 15a. If such states occur, processing of the output signals from mean value memory 7 is blocked via the inverting input of an AND gate 16 inserted into the corresponding output of mean value memory 7. At the same time, an additional OR gate 17 in the reset line of mean value memory 7 causes the latter to be reset to its starting state.

In the above-described storage of the actual systolic intervals during spontaneous action, the control is effected on the basis of the stored values during stimulation monitored by an additionally provided computer 12 which, actuated by a new interval signal recorded in the heart, is able to additionally change the associated base rate in memory 11 on the basis of additional information and values put in by communications unit 3, with access to memory 9 being possible. This change resides, in particular, in the provision of a correction value which, if the base rate of the pacemaker is regulated under stimulation conditions and the corresponding intervals during spontaneous action are evaluated, considers the change in the systolic intervals resulting due to the change in these conditions for the heart. Moreover, interpolation or compensation of the resulting frequency jumps can be compensated out in adjacent memory locations. Additionally, limit values for the stimulation frequencies can be programmed into memory 18 by way of communication unit 3 which values are not exceeded when the pacemaker base rate is adjusted. The corresponding limit value memory 18 is read by the computer 12 and if the respective value is exceeded due to regulation on the basis of the systolic intervals, a correction is made of the frequency value taken over into base rate memory 11.

Figure 1A:
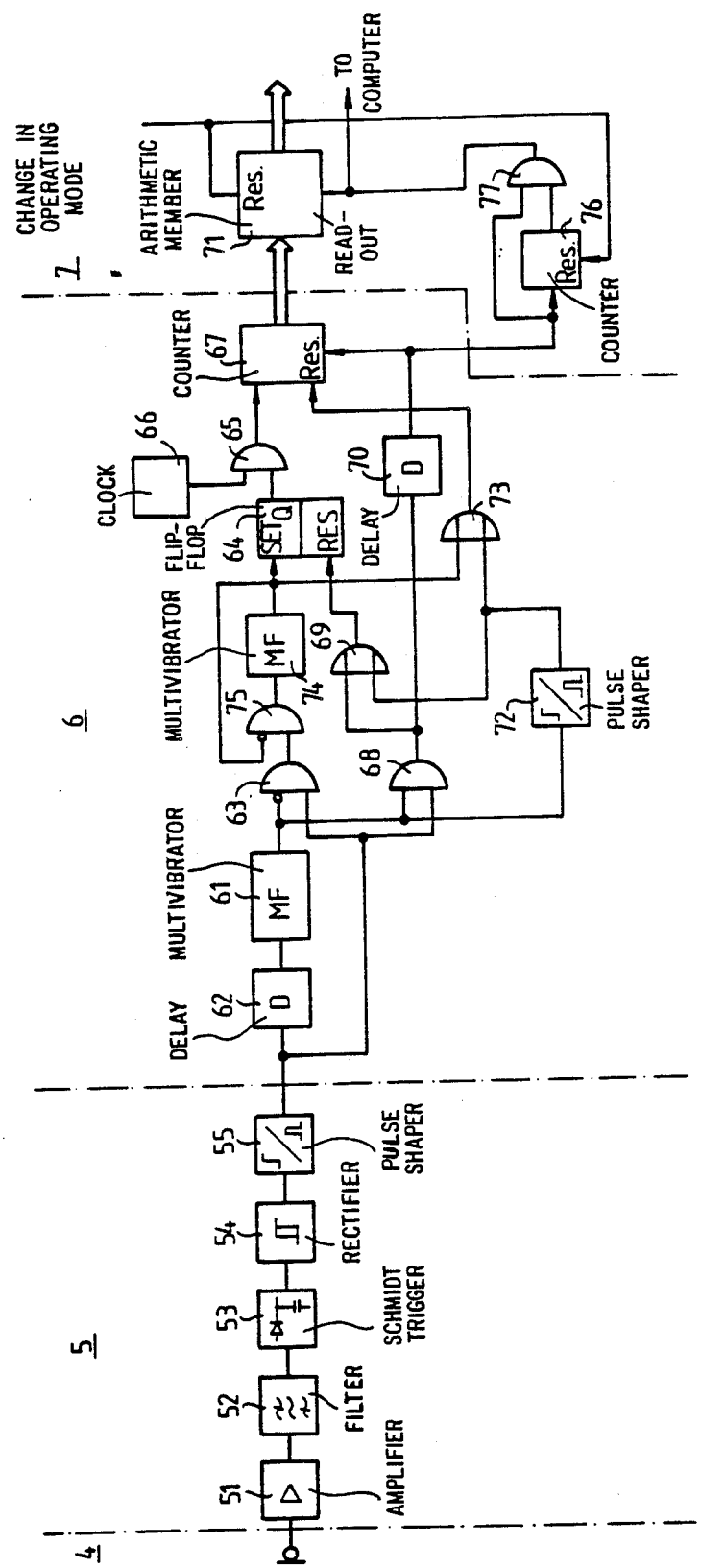
FIG. 1a, a detail view of the block circuit diagram of FIG. 1.

FIG. 1a is a detail view of the input portion of the circuit composed of modules 4 to 7. The processing group connected to microphone 4 is here composed of an input amplifier 51 to amplify the input signals, a filter 52 to filter out the frequency ranges characteristic of the systolic time intervals, a Schmitt trigger 53, a rectifier and filter member 54 for conversion of the frequency signals into pulses of one polarity, including a Schmitt trigger as threshold value discriminator, and a pulse shaper 55 for converting the leading edge of the output pulse of circuit 54 into a short control pulse.

Time evaluating member 6 is composed of a monostable multivibrator 61 which receives the output signal of stage 5 with a delay by a few milliseconds imparted by a delay member 62. The pulse duration of the monostable multivibrator 61 corresponds to the maximum systolic interval duration to be evaluated. If monoflop 61 is not set, the input signal passes through an AND gate 63 whose further (inverting) input is connected with the output of monoflop 61, to the "set" input of a flip-flop 64 which enables via its Q output an AND gate 65 so that a pulse signal generated by a clock pulse generator 66 reaches the corresponding input of a counter 67 so that the counter counts upward in correspondence with the expired time.

If monoflop 61 is set, the pulse terminating the systolic interval travels through an AND gate 68 and an OR gate 69 to the reset input of flip-flop 64 so that the counting process is interrupted. With a delay of a few milliseconds produced by a delay member 70, the "read-out" input of counter 67 is activated by the output of AND gate 68 so that the determined counter state is transferred to the subsequent mean memory 7. At the end of the pulse duration of monoflop 61 and after conversion of the trailing edge into a control pulse in a pulse converter 72, flip-flop 64 and counter 67 are reset via OR gates 73 and 69 without read-out taking place. By means of a further monoflop 74 which is inserted in the "set" line of flip-flop 64, the systolic time intervals are prevented from being evaluated in a sequence faster than what would correspond to the normal heart rate since an AND gate 75 in the input of monoflop 24 is blocked via its inverting input as long as the output pulse of monoflop 74 has not decayed. The pulse duration of monoflop 74 here corresponds to the maximum spacing between R waves of the corresponding heart frequency to be processed.

Mean value memory 7 includes an arithmetic member 71 that forms the mean value of the previously recorded systolic intervals (here: LVET) under priority consideration of the last five events and stores this value. If there is a change in the operating state or a transition from stimulating operation to the rest state of the pacemaker with existing sine rhythm, the arithmetic member 71 of the mean value memory is erased so that the mean value formation begins anew with the next systolic intervals recorded. Read-out from the mean value memory occurs with the input of every new mean value, after the latter has been processed. (Output: actuation of computer and activation of the output of the arithmetic member.) To reduce the frequency of changes in the stimulation frequency, the switching frequency can also be reduced by dividing it down. By means of a subsequently connected AND gate 77, a counter 76 blocks the output of determined interval values after, a change in operating state, since in this case counter 76 is set back ("reset" input) and emits an output signal to switch through AND gate 77 only if the counter state is $\geq 5$.

In the above-described storage of the actual systolic intervals during spontaneous action, the control is effected on the basis of the stored values during stimulation monitored by an additionally provided computer 12 which, actuated by a new interval signal recorded in the heart, is able to additionally change the associated base rate in memory 11 on the basis of additional information and values put in by communications unit 3, with access to memory 9 being possible. This change resides, in particular, in the provision of a correction value which, if the base rate of the pacemaker is regulated under stimulation conditions and the corresponding intervals during spontaneous action are evaluated, considers the change in the systolic intervals resulting due to the change in these conditions for the heart. Moreover, interpolation or compensation of the resulting frequency jumps can be compensated out in adjacent memory locations. Additionally, limit values for the stimulation frequencies can be programmed in by way of communications unit 3 which values are not exceeded when the pacemaker base rate is adjusted. The corresponding limit value memory 18 is read by the computer 12 and if the respective value is exceeded due to regulation on the basis of the systolic intervals, a correction is made of the frequency value taken over into base rate memory 11.

The remaining operating modes listed constitute memory operations with respect to memory 9, with time values for the escape intervals being stored in or read out from the memory, which is organized in the manner of a matrix, in dependence on the existing operational cases, for each individual memory location in dependence on the physiological parameter. This storing or reading out may possibly take place in separate, but otherwise parallel addressable memory locations for the operating states of "stimulated chamber action" and "spontaneous action". Correspondingly, if there are associated fixed difference values for the parameters, such a differentiation between the two operating states can also be effected by correspondingly influencing the parameter controlled addressing process. In the case of the exclusion of certain interval ranges, the interval values which are applicable instead - i.e. the limit interval values of the frequency ranges "excluded" during stimulation operation - are fed into the memory locations associated with the respective parameters.

Figure 2:
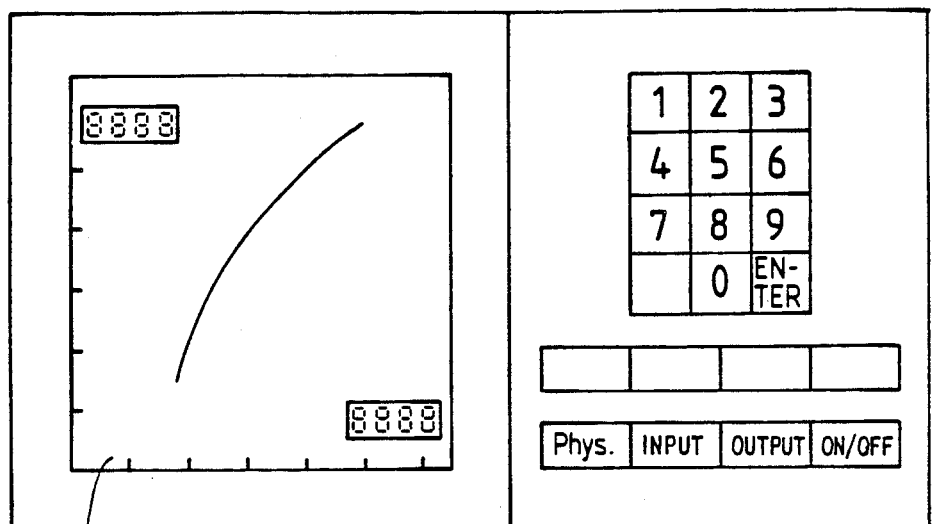
FIG. 2, a communication member for external interrogation and control of the pacemaker by the physician.

FIG. 2 is a top view of a control member 200 for external programming and control by the physician's hands. On display 201 in the left half of the Figure, the functional dependency of the heart frequency is shown in dependence on the systolic intervals to be detected, with the display being made separately (or superposed) for different operating states. The illustration corresponds to the values stored in pacemaker memory 9, with it being possible to either give a fixed functional relationship or the stimulation frequencies to be maintained for the systolic intervals determined in the implanted system are calculated on the basis of the values found when sine rhythms did exist. It is also possible to program in preferred stimulation frequencies to be maintained for predetermined value ranges of the systolic intervals as well as differences in the frequencies which belong to interval values for different operating modes, so that these correction values can be used when the mode is changed, etc. Processing of the heart and stimulation frequencies takes place in the form of the (reciprocal) interval between R waves so that proportionality with the detected interval times is attained with respect to processing and inverse relationships are avoided.

Figure 3:
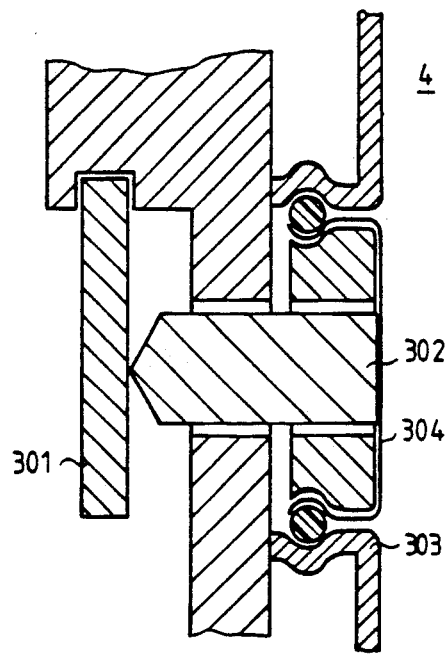
FIG. 3, an enlarged sectional view of an acoustic sensor.

The vibration pickup shown in FIG. 3 can be accommodated in the pacemaker itself as well as in the electrode which is anchored in the heart. It includes a unilaterally clamped in piezotransducer 301 which is in communication, via a mechanical coupling element 302, with a membrane 304 which seals off the housing and wall 303, respectively.

The invention in its embodiments is not limited to the above described, preferred embodiment. Rather, a number of variations are conceivable which utilize the illustrated solution even in basically different embodiments. In particular, the invention is not limited to realization with discrete logic components but can also be realized to advantage with programmed logic systems - preferably with the use of a microprocessor.

I claim:

1. A cardiac pacemaker for electrically stimulating the heart of a patient, comprising:
   electrode means for applying stimulation pulses to the heart of the patient;
   first monitoring means for detecting a physiological parameter which is characteristic of the patient and producing a first output signal representative of said first physiological parameter, said physiological parameter influencing spontaneous heart action in that the times between heart pulses spontaneously produced in the patient varies with variations in the value of said physiological parameter;
   second monitoring means for monitoring the times between heart pulses spontaneously produced in the patient and producing a second output signal representative thereof;
   memory means connected to said first and second monitoring means for storing representations based on said second output signal of the length of time between heart stimulation pulses spontaneously produced in the patient together with the concurrently occurring value of said physiological parameter;
   circuitry means for producing a first address signal to address said memory means as a function of said first output signal and for producing a third output signal corresponding to said length of time representation; and
   stimulation pulse producing means connected between said circuitry means and said electrode means for supplying to said electrode means, at least during the absence of spontaneous heart action, heart stimulation pulses at time intervals corresponding to said length of time representation produced by said circuitry means for the presently existing value of said physiological parameter.

2. Cardiac pacemaker according to claim 1 wherein said cardiac pacemaker is a demand pacemaker and the time between successive stimulation pulses is an escape interval.

3. Cardiac pacemaker according to claim 2 wherein the physiological parameter is a function of the heart frequency and of the manner of heart action initiation, and the escape interval is fixed by said circuitry means during a preceding spontaneous pulse, the preceding spontaneous pulse being a function of the physiological parameter values which correspond to operation without pacemaker intervention, and said escape interval is fixed during a preceding stimulation pulse, the preceding stimulation pulse being a function of value of said physiological parameter which correspond to operation with pacemaker intervention.

4. Cardiac pacemaker according to claim 3 wherein escape interval values for stimulation following spontaneous pulses and escape interval values for stimulation following stimulated pulses are caused to differ by said circuitry means by a fixed amount for at least one of said escape interval and the value of said physiological parameter.

5. Cardiac pacemaker according to claim 3 wherein the escape interval values for stimulation following spontaneous action and for stimulation following stimulated action are caused to differ by said circuitry means by a variable amount for at least one of the interval period and the parameter value when said escape intervals coincide.

6. Cardiac pacemaker according to claim 5 further comprising:
   correcting means for determining a correction value for various heart frequencies, said correction value being stored in said memory means to affect said third output signal produced by said circuitry means.

7. Cardiac pacemaker according to claim 6 wherein said correction value is supplied by an external programming means.

8. Cardiac pacemaker according to claim 6 wherein said correction value is determined by said correcting means during a transition between spontaneous and stimulated pulses, said correction value being based on said physiological parameter value during the transition.

9. Cardiac pacemaker according to claim 8 wherein said circuitry means automatically causes updating of a functional relationship in said memory means between the heart frequency and one of said physiological parameter and said correction value when spontaneous actions occur.

10. Cardiac pacemaker according to claim 9 wherein said physiological parameter and said escape interval are functionally related, said circuitry means causes said escape interval to be replaced when it falls outside of predetermined limits by at least one of (a) an upper interval limit value, (b) a lower interval limit value, and (c) values adjacent the upper and lower limit interval values.

11. Cardiac pacemaker according to claim 10 wherein the respective replaced values are determined by said circuitry means as a function of the direction of approach toward the limit values.

12. Cardiac pacemaker according to claim 11 wherein the predetermined time periods are caused to be replaced by said circuitry means in the absence of spontaneous heart action.

13. Cardiac pacemaker according to claim 1, wherein said physiological parameter is a function of at least one of a systolic interval, a QT interval and an electroplethysmographic signal.

14. Cardiac pacemaker according to claim 1 wherein the frequency of the stimulation pulses produced by said pulse producing means is caused by said circuitry means to be lower than the spontaneous stimulation frequency for a corresponding physiological parameter value.

* * * * *